United States Patent [19]

Steinberg et al.

[11] Patent Number: 5,746,748
[45] Date of Patent: May 5, 1998

[54] CIRCUMCISION INSTRUMENT

[75] Inventors: Frederic Steinberg, 40 Cooper Run Dr., Cherry Hill, N.J. 08003; Phyllis Adams, 12 Forestview Ct., Marlton, N.J. 08053; Frank W. Arnoth, Glen Mills, Pa.

[73] Assignees: Frederic Steinberg, Cherry Hill; Phyllis Adams, Marlton, both of N.J.

[21] Appl. No.: 579,330

[22] Filed: Dec. 27, 1995

[51] Int. Cl.$^6$ .................................. A61B 17/32
[52] U.S. Cl. ................... 606/118; 606/205; 606/206; 606/157; 81/418
[58] Field of Search .................... 606/118, 174, 606/157, 142, 1.9, 205, 206, 207; 81/418, 424.5, 318, 319, 324, 325, 338; 30/186, 175

[56] References Cited

U.S. PATENT DOCUMENTS

| | | | |
|---|---|---|---|
| 1,134,980 | 4/1915 | Pfeiffer, Jr. | 606/208 |
| 1,510,416 | 9/1924 | Pietz et al. | |
| 1,852,542 | 4/1932 | Sovatkin . | |
| 1,918,700 | 8/1933 | Harris | 606/118 |
| 2,025,345 | 12/1935 | Harris | 606/118 |
| 2,874,384 | 2/1959 | Krone | 606/158 |
| 2,962,024 | 11/1960 | Raymond | 606/208 |
| 3,013,560 | 12/1961 | Cohen . | |
| 3,176,689 | 4/1965 | Yahr | 81/318 |
| 3,277,895 | 10/1966 | Johnson | 128/325 |
| 3,510,923 | 5/1970 | Blake | 606/158 |
| 3,600,986 | 8/1971 | Baldwin, Jr. | 81/319 |
| 3,612,057 | 10/1971 | Freedman | 128/303 |
| 3,678,935 | 7/1972 | Bronstein | 128/325 |
| 3,698,395 | 10/1972 | Hasson | 128/155 |
| 3,874,389 | 4/1975 | Baumgarten | 128/346 |
| 3,892,242 | 7/1975 | Honjyo | 128/346 |
| 3,913,586 | 10/1975 | Baumgarten | 128/325 |
| 4,401,651 | 8/1983 | Knutson | 424/80 |
| 4,452,106 | 6/1984 | Tartaglia | 81/43 |
| 4,491,136 | 1/1985 | Leveen | 128/346 |
| 4,644,651 | 2/1987 | Jacobson | 30/251 |
| 4,648,401 | 3/1987 | Mattson | 128/305 |
| 4,686,983 | 8/1987 | Leisman et al. | 606/158 |
| 4,785,825 | 11/1988 | Romaniuk et al. | 606/174 |
| 5,152,774 | 10/1992 | Schroeder | 606/205 |
| 5,163,943 | 11/1992 | Mohiuddin et al. | 606/118 |
| 5,312,434 | 5/1994 | Crainich | 606/207 |
| 5,514,147 | 5/1996 | Hoskin et al. | 606/158 |

FOREIGN PATENT DOCUMENTS

| | | | |
|---|---|---|---|
| 390946 | 5/1923 | Germany | 606/158 |
| 2715324 | 10/1978 | Germany | 606/158 |

OTHER PUBLICATIONS

Al-Samarrai, A. Y. Izzidien, Plastibell Circumcision, J.R. Coll. Surg. Edinb., vol. 36 411 Dec. 1991.

Gelbaum, Ilene, Circumcision, Refining A Traditional Surgical Technique, J. of Nursery–Midwifery, vol. 38, No. 2 (Supplement) 18S–30S (Mar./Apr. 1993).

Primary Examiner—Robert A. Hafer
Assistant Examiner—Justine R. Yu
Attorney, Agent, or Firm—Morgan & Finnegan

[57] ABSTRACT

A circumcision instrument according to this invention comprises a pair of crossed members and a pivot pin fixed between the crossed members allowing for movement of the crossed members toward and away from each other about a common axis, wherein the crossed members further comprise a handle with a finger loop at the proximal end of the crossed members, a clamping tab extending from each finger loop, angular facets on the side of each clamping tab and a jaw at the distal end of the cross member with an upper surface providing a surface along which a cutting instrument may be moved to sever tissue clamped between the jaws wherein the lower surface of the jaws are partially cut away forming a clamping surface on the inner surface of the jaw wherein the jaws of the circumcision instrument close such that tissue is crushed without completely severing the tissue. The circumcision instrument of the present invention offers enhanced safety, simplicity, ease of use, cost effectiveness and reduced surgical time. The circumcision instrument of the present invention is meant to minimize potential complications during circumcision and maximize efficiency. The circumcision instrument according to this invention is also part of a sterile prepackaged circumcision kit for use during the circumcision procedure.

43 Claims, 4 Drawing Sheets

CIRCUMCISION INSTRUMENT

FIELD OF THE INVENTION

The present invention relates to surgical instruments generally and in particular to an improved instrument for use during the circumcision of male human beings.

BACKGROUND OF THE INVENTION

Circumcision, dating back to the Stone Age, is perhaps the oldest surgical procedure currently performed in the United States. At present, circumcision is statistically the most common operation performed in males with over 60% (>1,000,000) of American newborns circumcised annually.

Religious Circumcision has never been disputed. However, after World War II, opposition to routine non-religious circumcision began to surface. Specifically, in the 1970's and 1980's, routine newborn circumcision was not supported by certain members of the medical community for medical and cost reasons. Recently, however, the pendulum has begun to swing. In 1988, the American Academy of Pediatrics Task Force on circumcision indicated that newborn circumcision has potential medical benefits and advantages as well as disadvantages and risks.

Today, mounting evidence suggests the benefits to newborn circumcision. First, it should be noted that there are definite indications for circumcision, but none is present in the newborn. However, it is vital to conceptualize neonatal circumcision as an effective prophylactic tool for protecting the newborn male against potential penile morbidity during development and maturation, rather than curing a non-existent acute neonatal problem. Specifically, there is strong suggestive but inconclusive evidence that circumcision decreases the incidence of sexually transmitted diseases. There is also evidence suggesting that routine neonatal circumcision decreases the risk for contracting a urinary tract infection. More importantly, the current medical evidence strongly suggests that neonatal circumcision dramatically decreases the frequency of Posthitis, Balanitis, Phimosis and Paraphimosis later in life.

Thus, the increased frequency of urinary tract infections, Posthitis, Balanitis, Phimosis and Paraphimosis in uncircumcised males, both children and adults, is unacceptable if the etiology is simply failure to perform neonatal circumcision. Further weight can be given in support of neonatal circumcision if the only alternative is delayed circumcision—with its heightened morbidity, increased rate of complication, and elevated cost. Thus, the mounting studies supporting the benefits of circumcision suggest that the procedure should be regarded as an important prophylactic event in the development of American males, medically necessary, and cost-effective to a cost-conscious society.

With regard to the surgical technique, many methods are employed by those who perform circumcision, but five parameters are common to all:

(1) Asepsis;
(2) Adequate but not excessive removal of foreskin;
(3) Hemostasis;
(4) Protection of the glans; and
(5) Cosmetic acceptability.

There are five secondary parameters that are not common and are considered variables. These variables are based on the design of the circumcision instrument and the expertise of the surgical provider. These variables include:

(1) Enhanced procedural safety;
(2) Ease of use;
(3) Simplicity of design;
(4) Diminished surgical time; and
(5) Enhanced cost-effectiveness Generally, most surgical providers use the instrument with which they trained. However, prior instruments and devices used by these surgical providers have failed to optimize the above parameters and variables. Specifically, there is a need for a circumcision instrument capable of satisfying the above variables to add safety, speed, sophistication, and cost-efficiency into the circumcision procedure. For example, one variable, cost-effectiveness, is of critical importance in today's cost-conscious society. Many prior circumcision instruments are made of costly material requiring high labor costs for cleaning or resterilizing these instruments. Accordingly, there is a need for cost-effective circumcision instruments which can be disposable and made of less costly material including recyclable material. Additionally, several components, e.g., gauze, hemostats, cutting instruments, are necessary to complete the circumcision procedure. However, gathering, cleaning and resterilizing these components before performing each procedure is labor intensive and costly. Thus, there is also a need for a sterile prepackaged disposable circumcision kit.

Entry into the actual circumcision procedure, regardless of what technique or instrument is used, is usually similar, and may be referred to as the common entry path:

(1) The baby is placed in an infant restraint unit;
(2) Appropriate cleansing of the genitalia is performed;
(3) Appropriate drapes are applied;
(4) The tip of the foreskin is grasped on either side, with two hemostats, either curved or straight;
(5) A straight hemostat is then guided between the glans and the foreskin, opened and swept between 8 o'clock and 4 o'clock; This breaks any adhesions or other attachments; The first hemostat is then removed, and only its bottom jaw clamped to the tip of the foreskin at 8 o'clock; the bottom jaw of the second hemostat is clamped to the tip of the foreskin at 4 o'clock;
(6) The tissue is then crushed by closing the straight hemostat along the 12 o'clock zone in a vertical line; This will be referred to as the dorsal crush; and
(7) The dorsal crush is then cut with a cutting instrument such as a blade or scissors, allowing for visibility of the glans. This will be referred to as the dorsal slit.

At this point, the common entry path finalizes and each technique or instrument now assumes its own mode of circumcision.

There are three common techniques used in current practice—the Plastibell device, the Gomco clamp and the Mogen clamp.

The first common instrument for the removal of foreskin is the Plastibell device, a plastic bell with the groove close to the edge. See Al-Samarrai, A. Y. Izzidien, Plastibell Circumcision, *J. R. Coll. Surg. Edinb.*, Vol. 36, 411 (December 1991). In using the Plastibell device, the common entry path is first performed. When the dorsal crush is slit with scissors, the glans is exposed and the appropriate size of Plastibell is selected by fitting the bell over the glans so that it fits. After the bell is fitted over the glans, the prepuce is pulled back with two mosquito forceps. The ligature supplied with the Plastibell is applied around the groove of the bell and tied firmly, compressing the prepuce into the groove. The prepuce is trimmed with scissors, and the handle of the bell is broken off. After several days, the prepuce necrotizes and falls off. The plastic bell remains tied around the glans for days during the necrotic process.

There are several problems associated with the Plastibell device. First there are reports of the bell working its way into the penile shaft and of a permanent induced sulcus formed in the glans. Also there is some difficulty in correctly choosing the appropriate sized bell. Finally, some dexterity is required in tying the suture around the rim while holding the instrument. All of the above plus the many days necessary spent observing a necrosing prepuce leave much to be desired.

Another common instrument for the removal of foreskin is the Gomco clamp. See Gelbaum, Ilene, CIRCUMCISION, Refining a Traditional Surgical Technique, *J. of Nursery-Midwifery*, Vol. 38, No. 2 (Supplement) 18S–30S (March/April 1993). The Gomco clamp has a horizontal configuration consisting of 4 parts, a plate, bell, an arm and a nut and requires both assembly and disassembly. In using the Gomco clamp, the common entry path is first performed. When the crushed area of skin is slit with scissors, the glans is exposed and the appropriate size bell is selected by fitting the bell over the glans so that it fits. After the bell is fitted over the glans, the prepuce is pulled back with two mosquito forceps. The plate is then placed over the bell so that the prepuce is sandwiched between them. The arm is fitted into its proper place, and when the nut is secured in tightly, it exerts a crushing force on the prepuce at the junction of the bell and plate. The clamp is left on for 5 minutes to achieve hemostasis and the prepuce is excised.

There are several problems with the Gomco clamp. The relative sizes of the bell and hole in the plate are critical to proper performance of the clamp. The assembled clamp must be inspected before each use to ensure that (1) the plate is flat, (2) no light can be seen between the plate and bell, and (3) 0.085" of clearance is present between the arm and plate at the screw. Users are warned that clamps with worn, damaged, or missing parts should not be used. There are many reports which indicate that various parts of the clamp can be damaged or broken during use, resulting in inadequate skin-clamping force, and subsequent bleeding. Also part of the clamp can become worn or dislocated from long use or improper handling and cause inadequate clamping, crushing of the skin or inability to disassemble the clamp, all of which can result in significant injury to the patient.

Another circumcision instrument similar to the Gomco clamp is the Winkelmann clamp. See Saab, Basem Roberto, Hamadeh, Ghassan N., *The Journal of Family Practice*, Vol. 40, No. 2, 122 (Feb. 1995). The Winkelmann clamp is similar to the Gomco clamp but is made of 3 parts instead of 4, has a vertical configuration and does not require disassembling during the circumcision operation. However, the Winkelmann clamp still suffers from several of the problems associated with the Gomco clamp.

Another common circumcision instrument is the Mogen clamp. This device has a large shield which acts as a clamp. A latch hinged to one jaw of the shield is used to tighten the jaws to each other after placement on the tissue. The common entry path is first performed except that the dorsal crush and dorsal slit is usually skipped over. The clamp is simply placed at a pre-judged area considered to be both safe and adequate relative to the amount of foreskin to be removed. The latch is then secured. A blade is used to cleanly remove the excess foreskin by cutting directly on the flat surface of the shield. After a short interval to assume hemostasis, the latch is released and the clamp removed. The remaining tissue, which has been sealed by the crush, is then forcefully pushed back over the glans, completing the procedure.

There are two major problems associated with the Mogen clamp. First, the width of the instrument completely obliterates vision of all tissue beneath its surface. With the glans completely out of sight, there is a chance that the tip of the glans might be caught in the clamp. The second major problem is that the configuration of the tool makes its use clumsy to one who is inexperienced. Thus, the difficulty in learning and using the instrument, in addition to the visual loss after application, limits its popularity.

There are several other circumcision devices in the art as evidenced, for example, by U.S. Pat. Nos. 3,913,586, 5,163,943, 3,277,895 and 3,013,560. However, none of these above devices or patents taken either alone or in combination, is seen to describe the instant invention as claimed.

SUMMARY OF THE INVENTION

Objects and advantages of the invention are set forth below.

It is a principle object of the present invention to provide a novel circumcision instrument offering enhanced procedural safety, simplicity, ease of use, cost effectiveness and reduced surgical time.

It is a further object of the present invention to provide a circumcision instrument which is meant to minimize potential complications and maximize efficiency.

It is a further object of the present invention to provide a circumcision instrument which (1) is configured for comfort, i.e., scissors-like or hemostat-like in appearance and in application, (2) is a single unit and can be produced cheaply, (3) does not require assembly or disassembly, (4) application to tissue does not obstruct vision, (5) other than the basics necessary to perform the common entry pathway, no further skills are necessary for its usage, (6) is simple to learn to use regardless of previous surgical training because of familiarity with configurations similar to the circumcision instrument, i.e., scissors and hemostats, (7) allows the circumcision procedure to be done rapidly without sacrificing surgical quality, (8) in its simplicity, minimizes technical errors, i.e, complications, (9) maximizes cost effectiveness because it can be done quickly and safely, without assembly and disassembly, under direct vision and by non-physician surgical providers, (10) can be used in an office setting, further reducing cost, (11) can be used for post-neonatal circumcision, and (12) is cosmetically appealing.

It is still a further object of the present invention to provide a circumcision instrument which can be made of less costly material including material which is recyclable. It is another object of the present invention to provide a low cost disposable circumcision instrument which is part of a sterile prepackaged circumcision kit.

Accordingly, the circumcision instrument of the present invention comprises a pair of crossed members, a pivot pin fixed between the crossed members allowing for movement of the crossed members toward and away from each other around a common axis, the crossed members having two handles with finger loops at the proximal end of each crossed member, with a clamping tab extending from each finger loop such that the clamping tabs will overlap as the handles are closed. The side of each clamping tab that faces the opposite clamping tab contains sets of angular facets arranged in such a manner that the two clamping tabs will lock together as the angular facets engage. In a preferred embodiment, the clamping tabs contain three sets of angular facets. When the two handles have been closed and locked together by the action of these clamping tabs, the handles may be released by manipulating the finger loops in such a way as to separate the interlocking clamping tabs, thereby releasing them.

According to the invention, the distal end of the crossed members of the circumcision instrument further comprise jaws whose narrow width clamping surfaces act to clamp and pinch or crush any tissue between the jaws without completely severing it. To accomplish the narrow width of the clamping surfaces, the lower surface of the jaws are partially cut away forming the clamping surfaces on the inner side of the jaws. In one embodiment of the present invention, the clamping surfaces close with an approximately parallel gap such that tissue is crushed without completely severing the tissue. The upper surface of the jaws provides a smooth grinding surface along which a cutting instrument such as a scalpel or blade may be moved to sever the tissue which has been clamped between the jaws. In one embodiment of the present invention, the upper surfaces of the jaws are machined flat. In a preferred embodiment, the reduced area of the lower surface of the jaw is a curved, partially cylindrical area that leads to a wider area at a distance from the clamping surface and wherein the upper surface of the jaw is machined flat at a 90° angle to the clamping surface.

Further objects and advantages of the invention will become apparent from the following description taken in conjunction with the accompanying drawings.

DETAILED DESCRIPTION OF THE INVENTION

Figure 1:
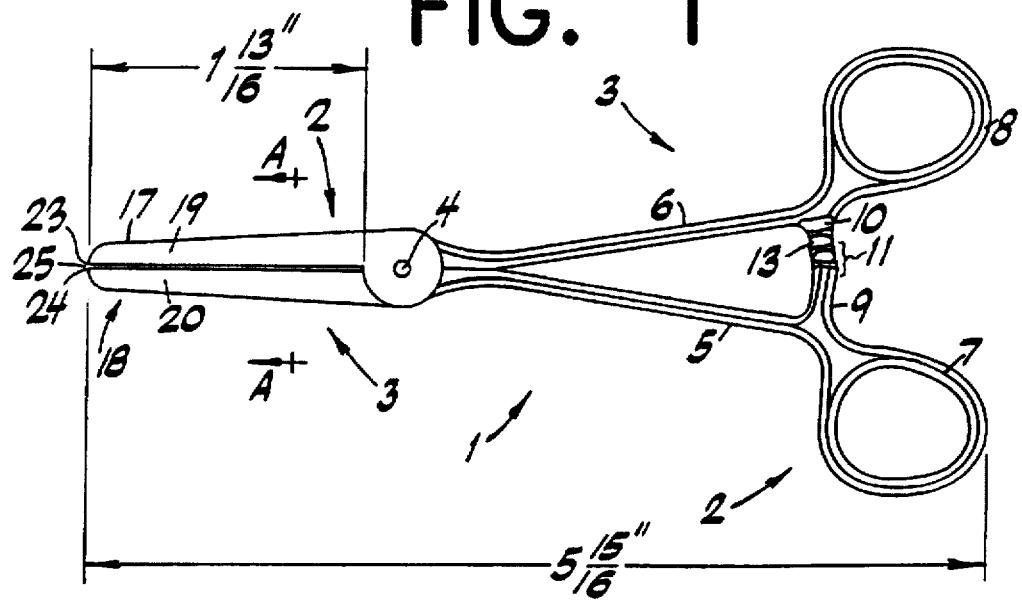
FIG. 1 is a top view of a circumcision instrument, as used during the circumcision procedure, in accordance with the present invention.

The circumcision instrument of the present invention comprises a scissors-like tool which functions as a hemostat. The nature of the design herein permits immediate familiarity to the novice.

In performing the circumcision procedure using the circumcision instrument of the present invention, steps (1)–(5) of the common entry path, as outlined above, are first performed. The two hemostats attached at the 4 o'clock and 8 o'clock position are pulled backed creating tension along the foreskin. The straight hemostat is then inserted inside the foreskin at the 12 o'clock position to a point just above the glans. The tissue is then crushed forming a dorsal crush. With the tension still provided by the first two hemostats at the 4 o'clock and 8 o'clock position, the straight hemostat is used to make a horizontal mark across the entire width of the foreskin. This horizontal mark is made perpendicular to the dorsal crush, slightly above the end of the dorsal crush. The circumcision instrument of the present invention is then placed along the horizontal mark, across the entire width of the foreskin. The foreskin is then crushed by the circumcision instrument of the present invention for approximately one minute. The first two hemostats at the 4 o'clock and 8 o'clock position are then removed. A cutting instrument such as a blade or scalpel is used to cleanly remove the excess foreskin by cutting directly on the upper surface of the circumcision instrument. After a short interval of approximately 30 seconds to assure hemostasis, the circumcision instrument is removed. The remaining tissue, which has been sealed by the crush, is then forcefully pushed back over the glans, completing the procedure.

The advantage of this procedure, using the circumcision instrument of the present invention, should be readily apparent over the prior art by those skilled in the art. First, prior devices require the dorsal crush to be cut forming the dorsal slit. This is necessary, for example, during operation of the Gomco clamp and Plastibell device, to provide room to insert the bell over the glans. However, in this procedure, it is necessary to insert the hemostat inside the foreskin past the tip of the glans to make the dorsal crush. This leads to the possibility of injury to the glans. Second, the design of the circumcision instrument of the present invention makes the circumcision procedure safe, easy to use and free from the possibility of the complications associated with prior devices. For example, prior devices require dexterity in manipulating the instruments. However, the circumcision instrument of the present invention can be easily manipulated by the surgical provider because of its scissor-like configuration. This novel configuration is extremely valuable in acquiring familiarity with the device because surgical providers are readily acquainted with scissors-like configurations, i.e. hemostats, but are generally unfamiliar with the configuration of the prior circumcision devices. Additionally, the configuration of the circumcision instrument of the present invention allows for clear visibility of the whole procedure, dramatically decreasing the chance of complications.

The structure of the circumcision instrument and its method of use will be more specifically explained by reference to the several figures of drawings attached hereto.

Figure 2:
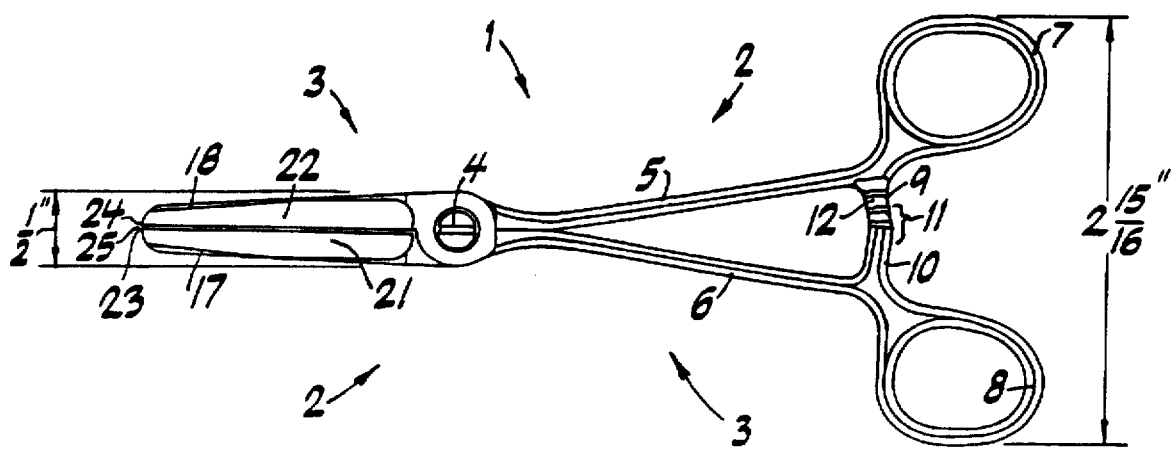
FIG. 2 is a bottom view of a circumcision instrument, as used during the circumcision procedure, in accordance with the present invention.
Figure 3:
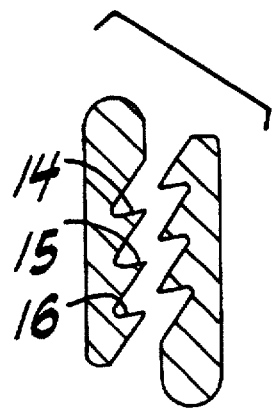
FIG. 3 is a view of the angular facets contained on a clamping tab extending from each finger loop on a circumcision instrument in accordance with the present invention.

Referring to FIGS. 1 and 2, the circumcision instrument is generally designated numeral 1. The circumcision instrument 1 comprises a pair of crossed members 2 and 3 and a pivot pin 4 fixed between the crossed members. The pivot pin 4 is defined as any means allowing for movement of crossed members 2 and 3 toward and away from each other about a common axis. The crossed members 2 and 3 comprise two handles 5 and 6 with finger loops 7 and 8 at the proximal end of crossed members 2 and 3. Clamping tabs 9 and 10 extend from each finger loop 7 and 8 in such a way that the clamping tabs 9 and 10 will overlap as the handles 5 and 6 are closed 11. The side of each clamping tab 9 and 10 that faces the opposite tab contains sets of angular facets 12 and 13 arranged in such a manner that the two clamping tabs 9 and 10 will lock together as the angular facets 12 and 13 engage. FIG. 3 illustrates a preferred embodiment comprising three sets of angular facets 14, 15 and 16 appearing on the side of each clamping tab 9 and 10. When handles 5 and 6 have closed and locked together by the action of the clamping tabs 9 and 10, the handles 5 and 6 may be released by manipulating the finger loops 7 and 8 in such a way as to separate the interlocking clamping tabs 9 and 10, thereby releasing them.

The distal end of each crossed member 2 and 3 of the circumcision instrument 1 comprises a jaw 17 and 18 each designed with upper surfaces 19 and 20 and lower surfaces 21 and 22. Upper surfaces 19 and 20 face the surgical provider during use of the circumcision instrument. The upper surfaces 19 and 20 of the jaws 17 and 18 provide a smooth flat grinding surface along which a cutting instrument such as a scalpel or a blade may be moved to sever the tissue which has been clamped between jaws 17 and 18. The lower surfaces 21 and 22 of jaws 17 and 18 are partially cut away forming narrow, flat, smooth clamping surfaces 23 and 24 of reduced area on the inner side of jaws 17 and 18. In a preferred embodiment of the present invention, the upper surfaces 19 and 20 are machined flat and the clamping surfaces 23 and 24 are at a 90° angle to the upper surfaces 19 and 20. The clamping surfaces 23 and 24 act to clamp and pinch or crush any tissue between the clamping surfaces 23 and 24, without completely severing the tissue. In one embodiment of the present invention, the jaws 17 and 18 are formed such that there is an approximately parallel gap 25 between the clamping surfaces 23 and 24 when the clamping surfaces 23 and 24 are fully closed and locked. In one embodiment of the present invention, clamping surfaces 23 and 24 of jaws 17 and 18 close with an approximately parallel gap 25 of about 0.006–0.012 inch between them when handles 5 and 6 are fully closed and locked.

Figure 4:
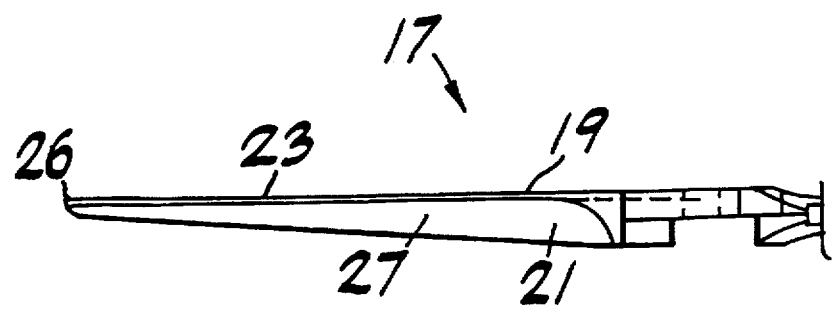
FIG. 4 is a side view of a jaw surface of the circumcision instrument in accordance with the present invention.
Figure 5:
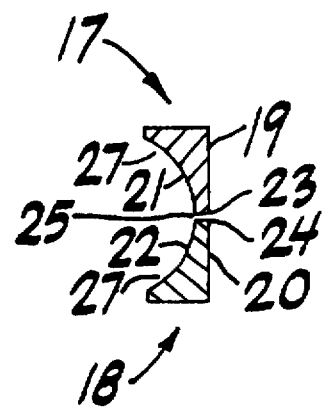
FIG. 5 is a cross-sectional view of the jaws taken along line A—A of FIG. 1.

Referring to FIG. 4, a side view of jaw 17, to accomplish the narrow width of the clamping surface 23, the lower surface 21 of the jaw 17 is partially cut away forming the clamping surface 23 on the inner side of jaw 17. Additionally, referring to FIG. 4, in a preferred embodiment of the present invention, the width of the clamping surface 23 is about 0.020–0.025 inch 26. Referring to FIG. 5, a cross-sectional view of jaws 17 and 18 taken along line A—A of FIG. 1, in a preferred embodiment, the lower surfaces 21 and 22 of each jaw 17 and 18 are partially cut away, presenting a reduced area comprising a curved, partially cylindrical surface 27 that leads to a wider area at a distance from the clamping surfaces 23 and 24.

Figure 8:
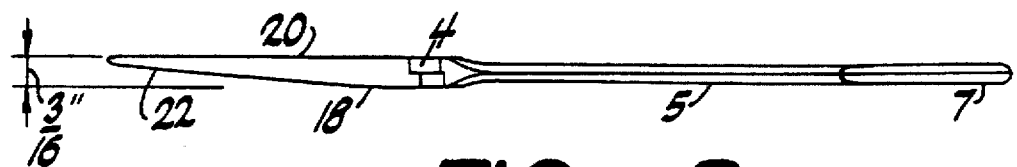
FIG. 8 is a side view of a circumcision instrument in accordance with the present invention.
Figure 6:
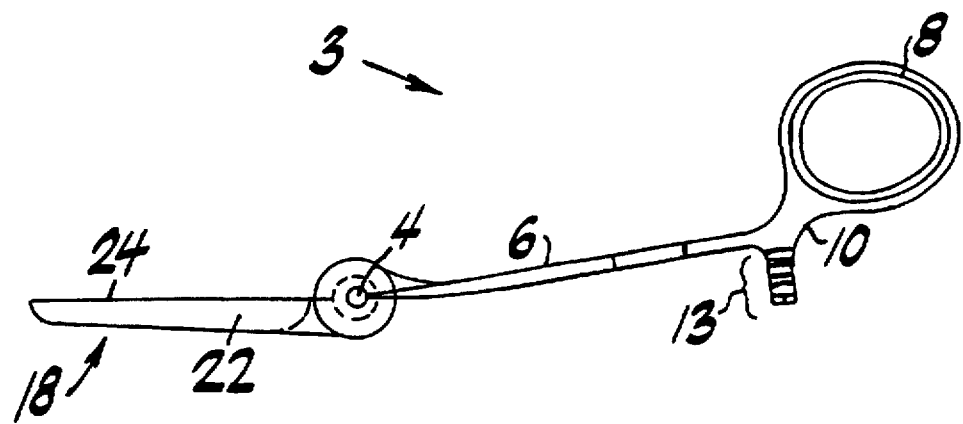
FIG. 6 is a top view of the upper half of a crossed member of a circumcision instrument in accordance with the present invention.
Figure 7:
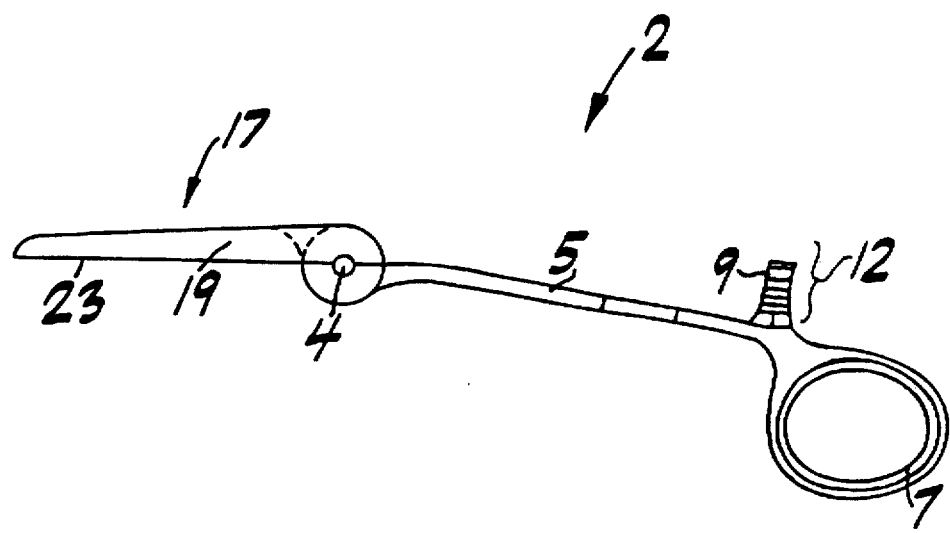
FIG. 7 is a top view of the lower half of a crossed member of a circumcision instrument in accordance with the present invention.

FIGS. 6 and 7 illustrate a top view of the upper and lower halfs of crossed members 2 and 3 with the corresponding features identified in FIGS. 1 and 2. FIG. 8 illustrates a side view of a circumcision instrument 1 with the corresponding features identified in FIGS. 1 and 2.

In a preferred embodiment of the present invention, the dimensions of the circumcision instrument 1 are as follows. Referring to FIG. 1, the length of each crossed member 2 and 3 is 5¹⁵⁄₁₆ inch. Referring to FIG. 2, the distance from one end of the finger loop 7 to the other end of the finger loop 8 when the handles are closed at the first angular facet is 2¹⁵⁄₁₆ inch. Referring to FIG. 8, the height of the jaw 18 is ³⁄₁₆ inch. Referring to FIG. 2, the length from one side of jaw 17 to the other side of jaw 18 is ½ inch. Referring to FIG. 1 the length of clamping surfaces 23 and 24 is 1¹³⁄₁₆ inch.

The circumcision instrument 1 may be made of any material suitable for use in surgical procedures. In one embodiment of the present invention, the circumcision instrument is made from a stainless steel alloy. In another embodiment, the circumcision instrument 1 of the present invention is made from a stainless steel alloy, 17-4PH.

In a further embodiment of the present invention, the circumcision instrument 1 may be made of an inexpensive disposable material, including material which may recyclable. For example, the circumcision instrument 1 can be made out of a combination of (1) any plastic resin and (2) a filler, which provides a high degree of stiffness. As is known by those skilled in the art, the term plastic resin comprises polymers. Examples of plastic resins include Acetal, liquid crystal polymers, nylon such as Nylon 66, Polycarbonate, Polyphenylene/Ether/Oxide (PPO/PPE) and Polyphenylene/Ether/Sulfide. Examples of suitable fillers include chopped glass fibers, chopped carbon fillers and mineral or ceramic particulate reinforcements. The circumcision instrument 1 of the present inventions made from these materials can be manufactured via a cost efficient injection molding process known to those skilled in the art providing a low cost disposable circumcision instrument.

Figure 9:
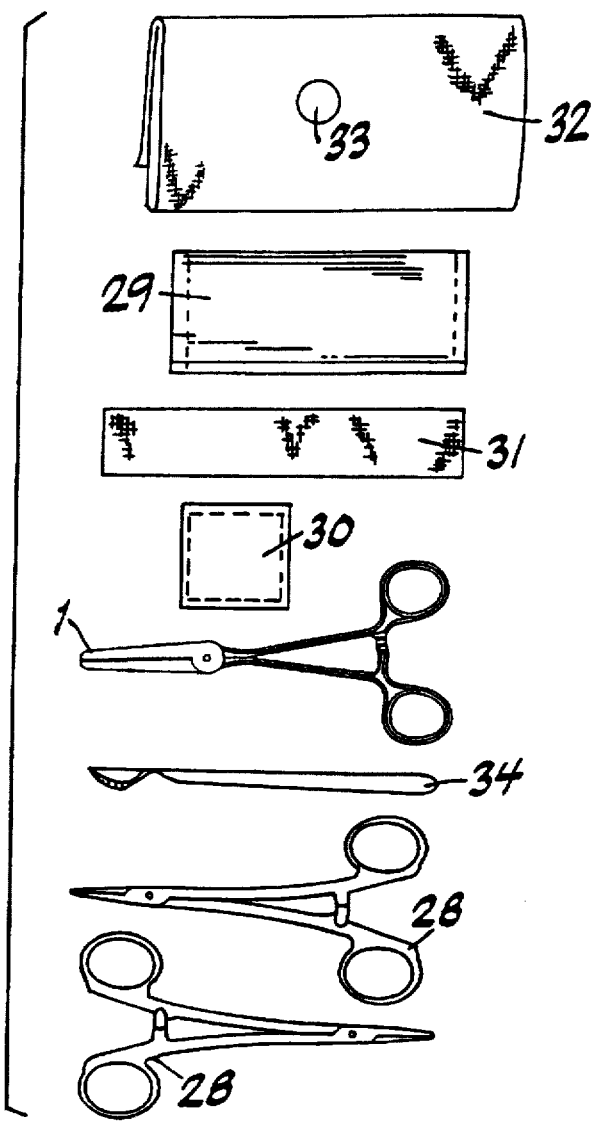
FIG. 9 shows components of a sterile prepackaged circumcision kit.

In another embodiment of the invention, the circumcision instrument 1 of the present invention is part of a sterile prepackaged circumcision kit. Referring to FIG. 9, the sterile prepackaged circumcision kit comprises all the necessary components for completing the circumcision procedure using the circumcision instrument 1 of the present invention including: (1) hemostats 28; (2) antibacterial cleanser 29; (3) circumcision instrument 1 of the present invention; (4) gauze pads 30; (5) post-operative dressing 31; (6) a drape 32 with a hole 33 isolating the penis and scrotal area; and (7) a cutting instrument 34. In one embodiment of the present invention, the sterile prepackaged circumcision kit of the present invention comprises (1) 3 hemostats; (2) BETADINE®; (3) the circumcision instrument 1 of the present invention; (4) gauze pads; (5) vaseline gauze pads; (6) a drape; and (7) a blade or scalpel. In the preferred embodiment, the sterile prepackaged circumcision kit of the present invention is disposable comprising (1) 3 disposable hemostats; (2) BETADINE®; (3) a disposable circumcision instrument 1 of the present invention; (4) gauze pads; (5) vaseline gauze pads; (6) a drape; and (7) a blade or scalpel.

Figure 10:
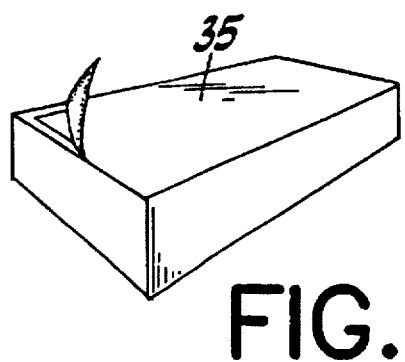
FIG. 10 is a box which contains the components of a sterile prepackaged circumcision kit.

FIG. 10 illustrates a box 35 which contains the components of the sterile prepacked circumcision kit. In one embodiment of the present invention, the box 35 has a pull off sealed top.

The use of the sterile prepackaged circumcision kit in accordance with present invention is a low cost and time-saving alternative to present circumcision procedures. Specifically, the sterile prepackaged circumcision kit of the present invention allows for a convenient cost-effective unit which does not involve the labor costs of having medical personnel prepare, clean and resterilize the components necessary for completing the circumcision procedure. According to the present invention, the sterile prepackaged circumcision kit contains all the necessary components for completing the circumcision procedure of the present invention in one unit which can simply be discarded upon completion of the circumcision procedure. Additionally, to provide added cost savings, the components can be recycled upon completion of the circumcision procedure.

The above described preferred embodiments are intended, by way of example, to illustrate the principles of the invention but not to limit the scope of the claims. Various other embodiments and modifications to these preferred embodiments may be made by those skilled in the art without departing from the scope of the following claims.

What is claimed is:

1. A circumcision instrument comprising:
   a pair of crossed members having proximal ends and distal ends; and
   a pivot pin fixed between the crossed members allowing for movement of the crossed members toward and away from each other;
   the crossed members comprising
      handles with finger loops at the proximal ends of the crossed members;
      clamping tabs extending from the finger loops wherein the clamping tabs will overlap when the handles are closed and wherein angular facets are formed on the clamping tabs such that the clamping tabs will lock together as the angular facets engage; and
      jaws on the distal ends of the crossed members having upper surfaces and lower surfaces wherein the upper surfaces of the jaws provide surfaces along which a cutting instrument is moved to sever tissue clamped between the jaws and wherein the lower surfaces of the jaws are partially cut away forming clamping surfaces of reduced area on inner sides of the jaws whereby the clamping surfaces act to crush tissue between the clamping surfaces without severing the tissue when the handles are fully closed.

2. A circumcision instrument according to claim 1 wherein the upper surfaces of the jaws are machined flat and wherein the clamping surfaces are at a 90° angle to the flat upper surfaces of the jaws.

3. A circumcision instrument according to claim 2 wherein the lower surfaces of the laws are partially cut away providing curved, partially cylindrical surfaces.

4. A circumcision instrument according to claim 3 wherein the circumcision instrument is made of a plastic resin and a filler.

5. A circumcision instrument according to claim 3 wherein the clamping surfaces form an approximately parallel gap between the clamping surfaces when the handles are fully closed.

6. A circumcision instrument according to claim 5 wherein the clamping tabs contain three angular facets, the clamping surfaces form an approximately parallel gap of about 0.006–0.012 inch and the clamping surfaces have a width of about 0.020–0.025 inch.

7. A circumcision instrument according to claim 5 wherein the circumcision instrument is made of a stainless steel alloy.

8. A circumcision instrument according to claim 5 wherein the circumcision instrument is made of a plastic resin and a filler.

9. A circumcision instrument according to claim 6 wherein the circumcision instrument is made of a stainless steel alloy.

10. A circumcision instrument according to claim 6 wherein the circumcision instrument is made of a plastic resin and a filler.

11. A circumcision instrument according to claim 2 wherein the clamping surfaces form an approximately parallel gap between the clamping surfaces when the handles are fully closed.

12. A circumcision instrument according to claim 4 wherein the clamping tabs contain three angular facets, the clamping surfaces form an approximately parallel gap of about 0.006–0.012 inch and the clamping surfaces have a width of about 0.020–0.025 inch.

13. A circumcision instrument according to claim 12 wherein the circumcision instrument is made of a stainless steel alloy.

14. A circumcision instrument according to claim 12 wherein the circumcision instrument is made of a plastic resin and a filler.

15. A circumcision instrument according to claim 11 wherein the circumcision instrument is made of a stainless steel alloy.

16. A circumcision instrument according to claim 11 wherein the circumcision instrument is made of a plastic resin and a filler.

17. A circumcision instrument according to claim 2 wherein the circumcision instrument is made of a stainless steel alloy.

18. A circumcision instrument according to claim 3 wherein the circumcision instrument is made of a stainless steel alloy.

19. A circumcision instrument according to claim 2 wherein the circumcision instrument is made of a plastic resin and a filler.

20. A circumcision instrument according to claim 1 wherein the circumcision instrument is made of a stainless steel alloy.

21. A circumcision instrument according to claim 1 wherein the circumcision instrument is made of a plastic resin and a filler.

22. A sterile prepackaged circumcision kit comprising a hemostat, an antibacterial cleanser, gauze pads, post operative dressing, a drape, a tissue cutting instrument and a circumcision instrument, the circumcision instrument comprising:
   a pair of crossed members having proximal ends and distal ends; and
   a pivot pin fixed between the crossed members allowing for movement of the crossed members toward and away from each other;
   the crossed members comprising
      handles with finger loops at the proximal ends of the crossed members;
      clamping tabs extending from the finger loops wherein the clamping tabs will overlap when the handles are closed and wherein angular facets are formed on the clamping tabs such that the clamping tabs will lock together as the angular facets engage; and
      jaws on the distal ends of the crossed members having upper surfaces and lower surfaces wherein the upper surfaces of the jaws provide surfaces along which a cutting instrument is moved to sever tissue clamped between the jaws and wherein the lower surfaces of the jaws are partially cut away forming clamping surfaces of reduced area on inner sides of the jaws whereby the clamping surfaces act to crush tissue between the clamping surfaces without severing the tissue when the handles are fully closed.

23. The sterile prepackaged circumcision kit according to claim 22 having 3 hemostats and wherein the antibacterial cleanser is BETADINE®, the post operative dressing is a vaseline gauze pad and the tissue cutting instrument is a blade or scalpel.

24. The sterile prepackaged circumcision kit according to claim 23 where the circumcision instrument is made of a stainless steel alloy.

25. The sterile prepackaged circumcision kit according to claim 23 wherein the circumcision instrument is made of a plastic resin and a filler.

26. The sterile prepackaged circumcision kit according to claim 22 wherein the upper surfaces of the jaws of the circumcision instrument are machined flat and wherein the clamping surfaces of the circumcision instrument are at a 90° angle to the flat upper surfaces of the jaws.

27. The sterile prepackaged circumcision kit according to claim 26 having 3 hemostats and wherein the antibacterial cleanser is BETADINE®, the post operative dressing is a vaseline gauze pad and the tissue cutting instrument is a blade or scalpel.

28. The sterile prepackaged circumcision kit according to claim 27 having 3 hemostats and wherein the antibacterial cleanser is BETADINE®, the post operative dressing is a vaseline gauze pad and the tissue cutting instrument is a blade or scalpel.

29. The sterile prepackaged circumcision kit according to claim 27 wherein the clamping surfaces of the circumcision instrument form an approximately parallel gap between the clamping surfaces when the handles are fully closed.

30. The sterile prepackaged circumcision kit according to claim 29 having 3 hemostats and wherein the antibacterial cleanser is BETADINE®, the post operative dressing is a vaseline gauze pad and the tissue cutting instrument is a blade or scalpel.

31. The sterile prepackaged circumcision kit according to claim 29 wherein the clamping tabs of the circumcision instrument contain three angular facets, the clamping surfaces of the circumcision instrument form an approximately parallel gap of about 0.006 inch–0.012 inch and the clamping surfaces of the circumcision instrument have a width of about 0.020–0.25 inch.

32. The sterile prepackaged circumcision kit according to claim 31 having 3 hemostats and wherein the antibacterial-cleanser is BETADINE®, the post operative dressing is a vaseline gauze pad and the tissue cutting instrument is a blade or scalpel.

33. The sterile prepackaged circumcision kit according to claim 32 wherein the circumcision instrument is made of a stainless steel alloy.

34. The sterile prepackaged circumcision kit according to claim 32 where the circumcision instrument is made of a plastic resin and a filler.

35. The sterile prepackaged circumcision kit according to claim 31 where the circumcision instrument is made of a stainless steel alloy.

36. The sterile prepackaged circumcision kit according to claim 31 wherein the circumcision instrument is made of a plastic resin and a filler.

37. The sterile prepackaged circumcision kit according to claim 26 wherein the lower surfaces of the laws of the circumcision instrument are partially cut away providing curved, partially cylindrical surfaces.

38. The sterile prepackaged circumcision kit according to claim 26 wherein the clamping surfaces of the circumcision instrument form an approximately parallel gap between the clamping surfaces when the handles are closed.

39. The sterile prepackaged circumcision kit according to claim 38 having 3 hemostats and wherein the antibacterial cleanser is BETADINE®, the post operative dressing is a vaseline gauze pad and the tissue cutting instrument is a blade or scalpel.

40. The sterile prepackaged circumcision kit according to claim 38 wherein the clamping tabs of the circumcision instrument contain three angular facets, the clamping surfaces of the circumcision instrument form an approximately parallel gap of about 0.006 inch–0.012 inch and the clamping surfaces of the circumcision instrument have a width of about 0.020–0.25 inch.

41. The sterile prepackaged circumcision kit according to claim 40 having 3 hemostats and wherein the antibacterial-cleanser is BETADINE®, the post operative dressing is a vaseline gauze pad and the tissue cutting instrument is a blade or scalpel.

42. The sterile prepackaged circumcision kit according to claim 22 where the circumcision instrument is made of a stainless steel alloy.

43. The sterile prepackaged circumcision kit according to claim 22 wherein the circumcision instrument is made of a plastic resin and a filler.

* * * * *

UNITED STATES PATENT AND TRADEMARK OFFICE
CERTIFICATE OF CORRECTION

PATENT NO. : 5,746,748
DATED : May 5, 1998
INVENTOR(S) : Frederic Steinberg, Phyllis Adams and Frank W. Arnoth It is certified that error appears in the above-identified patent and that said Letters Patent is hereby corrected as shown below:

In claim 3, line 2 (col. 9, line 30), delete " laws" and insert --jaws --.

In claim 12, line 1 (col. 9, line 60), delete " 4" and insert -- 11 --.

In claim 23, lines 2-3 (col. 10, lines 53-54), delete " antibacterial cleanser is BETADINE®, the" .

In claim 27, lines 2-3 (col. 11, lines 2-3), delete " antibacterial cleanser is BETADINE®, the" .

In claim 28, line 2 (col. 11, line 7), delete " 27" and insert -- 37 --.

In claim 28, lines 2-3 (col. 11, lines 7-8), delete " antibacterial cleanser is BETADINE®, the" .

In claim 29, line 1 (col. 11, line 12), delete " 27" and insert -- 37 --.

In claim 30, lines 2-3 (col. 11, lines 16-17), delete " antibacterial cleanser is BETADINE®, the" .

UNITED STATES PATENT AND TRADEMARK OFFICE
CERTIFICATE OF CORRECTION

PATENT NO. : 5,746,748
DATED : May 5, 1998
INVENTOR(S) : Frederic Steinberg, Phyllis Adams and Frank W. Arnoth It is certified that error appears in the above-identified patent and that said Letters Patent is hereby corrected as shown below:

In claim 32, lines 2-3 (col. 11, lines 28-29), delete " antibacterial cleanser is BETADINE®, the" .

In claim 39, lines 2-3 (col. 12, lines 15-16), delete " antibacterial cleanser is BETADINE®, the" .

In claim 41, lines 2-3 (col. 12, lines 27-28), delete " antibacterial cleanser is BETADINE®, the" .

Signed and Sealed this

Twenty-second Day of December, 1998

Attest:

BRUCE LEHMAN

Attesting Officer

Commissioner of Patents and Trademarks